(12) United States Patent
Hernandez et al.

(10) Patent No.: US 10,682,143 B2
(45) Date of Patent: Jun. 16, 2020

(54) APPLICATORS FOR MODULAR MAGNETIC ANASTOMOSIS DEVICE

(71) Applicant: IRCAD, Strasbourg (FR)

(72) Inventors: Juan Hernandez, Strasbourg (FR); Michele Diana, Lingolsheim (FR)

(73) Assignee: IRCAD, Strasbourg (FR)

( * ) Notice: Subject to any disclaimer, the term of this patent is extended or adjusted under 35 U.S.C. 154(b) by 0 days.

(21) Appl. No.: 14/654,643

(22) PCT Filed: Dec. 20, 2013

(86) PCT No.: PCT/IB2013/003246
§ 371 (c)(1),
(2) Date: Jun. 22, 2015

(87) PCT Pub. No.: WO2014/102621
PCT Pub. Date: Jul. 3, 2014

(65) Prior Publication Data
US 2015/0342608 A1 Dec. 3, 2015

Related U.S. Application Data

(60) Provisional application No. 61/740,865, filed on Dec. 21, 2012, provisional application No. 61/794,782, filed on Mar. 15, 2013.

(51) Int. Cl.
*A61B 17/11* (2006.01)
*A61B 17/34* (2006.01)
(Continued)

(52) U.S. Cl.
CPC ...... *A61B 17/1114* (2013.01); *A61B 17/3421* (2013.01); *A61B 17/3468* (2013.01);
(Continued)

(58) Field of Classification Search
CPC ........... A61M 25/0009; A61B 17/1152; A61B 2017/348; A61B 2017/3482; A61B 2017/306; A61B 2017/3488
See application file for complete search history.

(56) References Cited

U.S. PATENT DOCUMENTS 4,197,840 A 4/1980 Beck et al.
5,667,488 A * 9/1997 Lundquist .......... A61B 10/0233
604/22
(Continued)

FOREIGN PATENT DOCUMENTS

EP 2086426 A2 8/2009
EP 2934347 A2 10/2015
(Continued)

OTHER PUBLICATIONS

PCT Patent Application No. PCT/IB2013/003246 International Search Report and Written Opinion dated Feb. 5, 2015.
(Continued)

*Primary Examiner* — Anh T Dang
(74) *Attorney, Agent, or Firm* — Wilson Sonsini Goodrich & Rosati

(57) ABSTRACT

The present disclosure provides description of applicators to implement modular magnetic anastomosis device. In one embodiment the delivery device is a laparoscopic instrument for MISS surgery, in another embodiment the delivery device is endoscopy or colonoscopy instrument for NOTES surgery.

10 Claims, 20 Drawing Sheets

(51) Int. Cl.
  *A61B 17/00* (2006.01)
  *A61B 17/30* (2006.01)

(52) U.S. Cl.
  CPC .............. *A61B 2017/00876* (2013.01); *A61B 2017/1117* (2013.01); *A61B 2017/1139* (2013.01); *A61B 2017/306* (2013.01); *A61B 2017/3484* (2013.01); *A61B 2017/3488* (2013.01)

(56) References Cited

U.S. PATENT DOCUMENTS

| | | | |
|---|---|---|---|
| 5,817,062 A * | 10/1998 | Flom | A61B 17/3417 604/174 |
| 5,891,159 A | 4/1999 | Sherman et al. | |
| 6,110,187 A | 8/2000 | Donlon | |
| 6,352,543 B1 | 3/2002 | Cole | |
| 8,092,378 B2 | 1/2012 | Roth et al. | |
| 2002/0147385 A1 | 10/2002 | Butler et al. | |
| 2005/0283235 A1 | 12/2005 | Kugler et al. | |
| 2006/0235368 A1 | 10/2006 | Oz | |
| 2006/0263145 A1 * | 11/2006 | Pal | A61F 2/95 403/1 |
| 2007/0135803 A1 * | 6/2007 | Belson | A61B 1/00154 606/1 |
| 2007/0167868 A1 * | 7/2007 | Sauer | A61B 10/0233 600/564 |
| 2007/0255165 A1 | 11/2007 | Uesugi et al. | |
| 2007/0276378 A1 | 11/2007 | Harrison et al. | |
| 2007/0299310 A1 * | 12/2007 | Phillips | A61B 1/04 600/127 |
| 2008/0161644 A1 | 7/2008 | Ghabrial | |
| 2008/0200933 A1 | 8/2008 | Bakos et al. | |
| 2009/0125042 A1 | 5/2009 | Mouw | |
| 2010/0076573 A1 | 3/2010 | Kugler et al. | |
| 2010/0161040 A1 * | 6/2010 | Braido | A61B 17/11 623/2.1 |
| 2011/0160752 A1 | 6/2011 | Aguirre | |
| 2011/0295285 A1 | 12/2011 | McWeeney et al. | |
| 2012/0197062 A1 | 8/2012 | Requarth | |
| 2013/0253550 A1 | 9/2013 | Beisel et al. | |
| 2015/0164508 A1 | 6/2015 | Hernandez et al. | |
| 2016/0022266 A1 | 1/2016 | Lukin et al. | |
| 2016/0262761 A1 | 9/2016 | Beisel et al. | |

FOREIGN PATENT DOCUMENTS

| | | |
|---|---|---|
| JP | 2006271832 A | 10/2006 |
| JP | 4681920 B2 | 5/2011 |
| WO | WO 98/02099 A1 | 1/1998 |
| WO | WO-2008061024 A2 | 5/2008 |
| WO | WO2009048954 A1 | 4/2009 |
| WO | WO 2014/102621 A2 | 7/2014 |

OTHER PUBLICATIONS

PCT Patent Application No. PCT/IB2013/003246 International Preliminary Report on Patentability dated Jul. 2, 2015.
Chinese Patent Application No. 201280040553.9 Office Action dated Oct. 29, 2015.
EP Patent Application No. 12811240.6 Extended European Search Report dated Jun. 9, 2015.
International Search Report and Written Opinion for PCT Patent Application No. PCT/US2012/046272 dated Oct. 1, 2012.
Jamshidi et al., Magnamosis: Magnetic compression anastomosis with comparison to suture and staple techniques. J.Pediatr. Surg., 44(1):222-228 (2009).
ROC (Taiwan) Patent Application No. 102147684 Office Action and Search Report dated Nov. 18, 2015.
U.S. Appl. No. 14/237,521 Office Action dated Sep. 29, 2015.
Chinese Patent Application No. 201280040553.9 Second Office Action dated Sep. 20, 2016.
Taiwan Patent Application No. 105126839 Office Action dated May 1, 2017.
U.S. Appl. No. 14/237,521 Office Action dated Dec. 1, 2016.
U.S. Appl. No. 14/237,521 Office Action dated Jun. 14, 2016.
European Patent Application No. 13861506.7 Communication dated Aug. 30, 2017.
U.S. Appl. No. 14/237,521 Office Action dated Jun. 16, 2017.
European Patent Application No. 19174351.7 Extended European Search Report dated Jul. 18, 2019.
U.S. Appl. No. 14/237,521 Final Office Action dated Mar. 7, 2019.
U.S. Appl. No. 14/237,521 Office Action dated May 10, 2018.

* cited by examiner

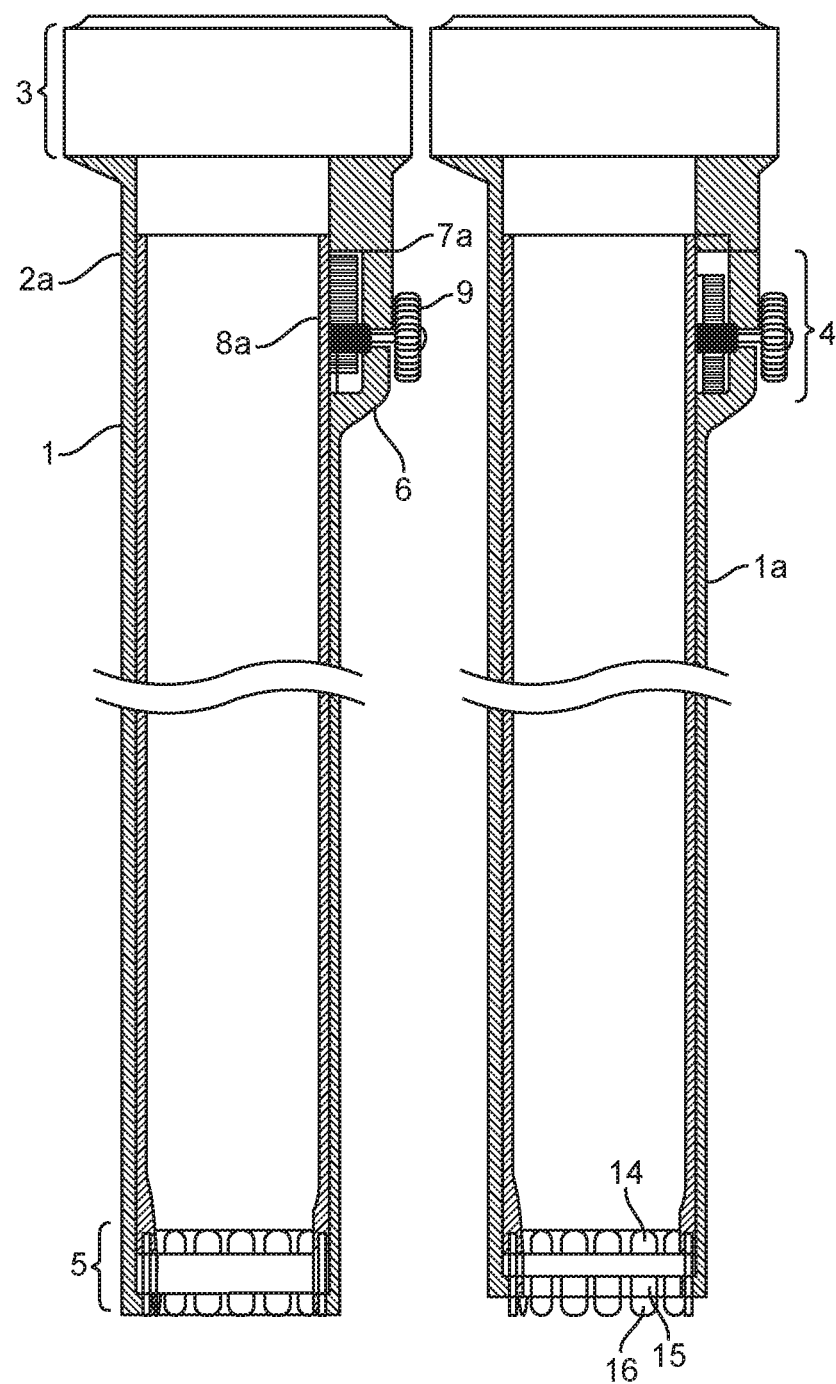
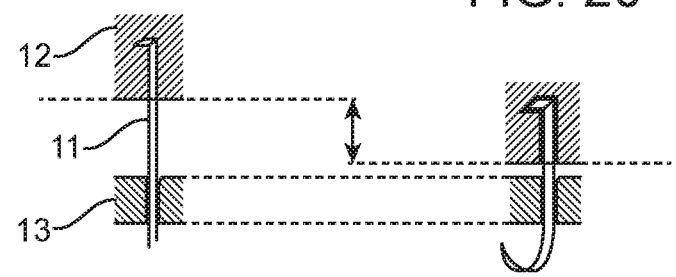
FIG. 19   FIG. 20
FIG. 21   FIG. 22

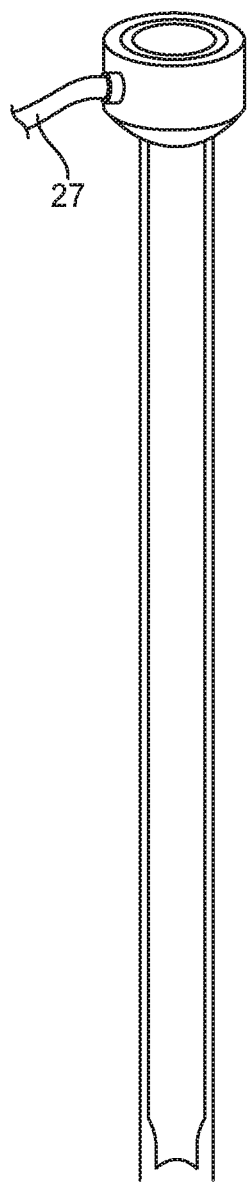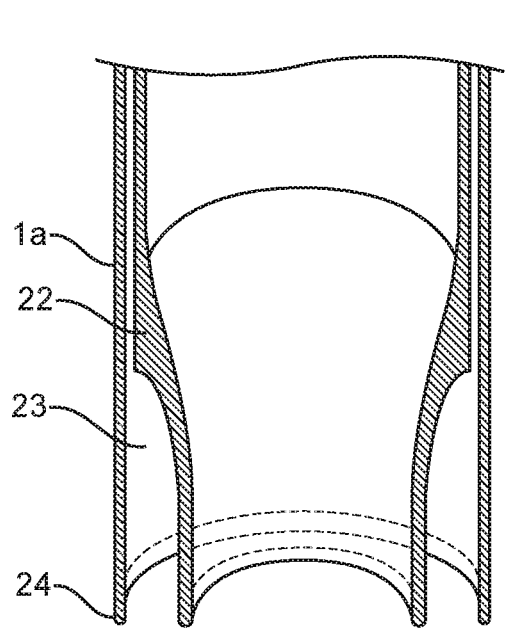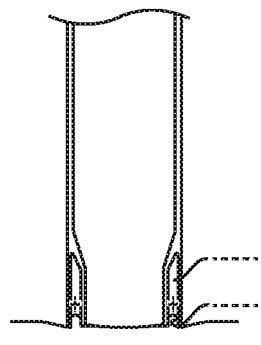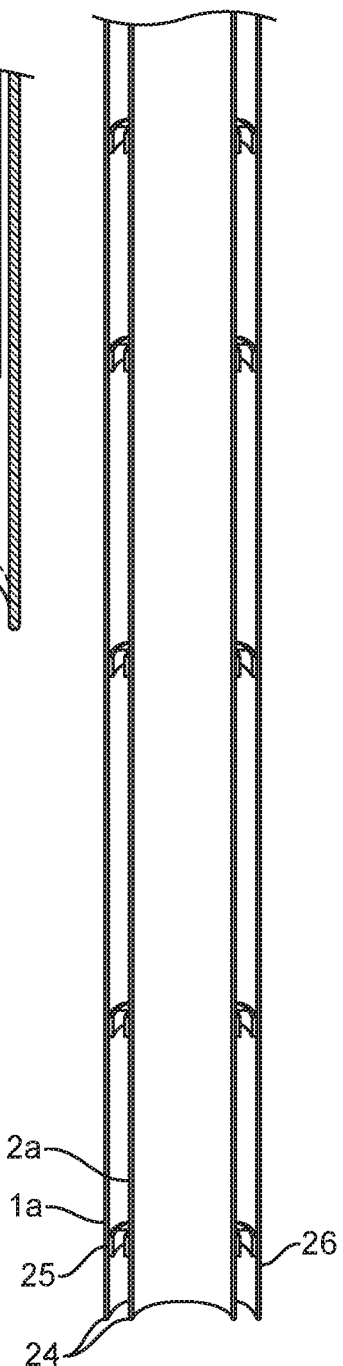
FIG. 26
FIG. 28
FIG. 27
FIG. 29

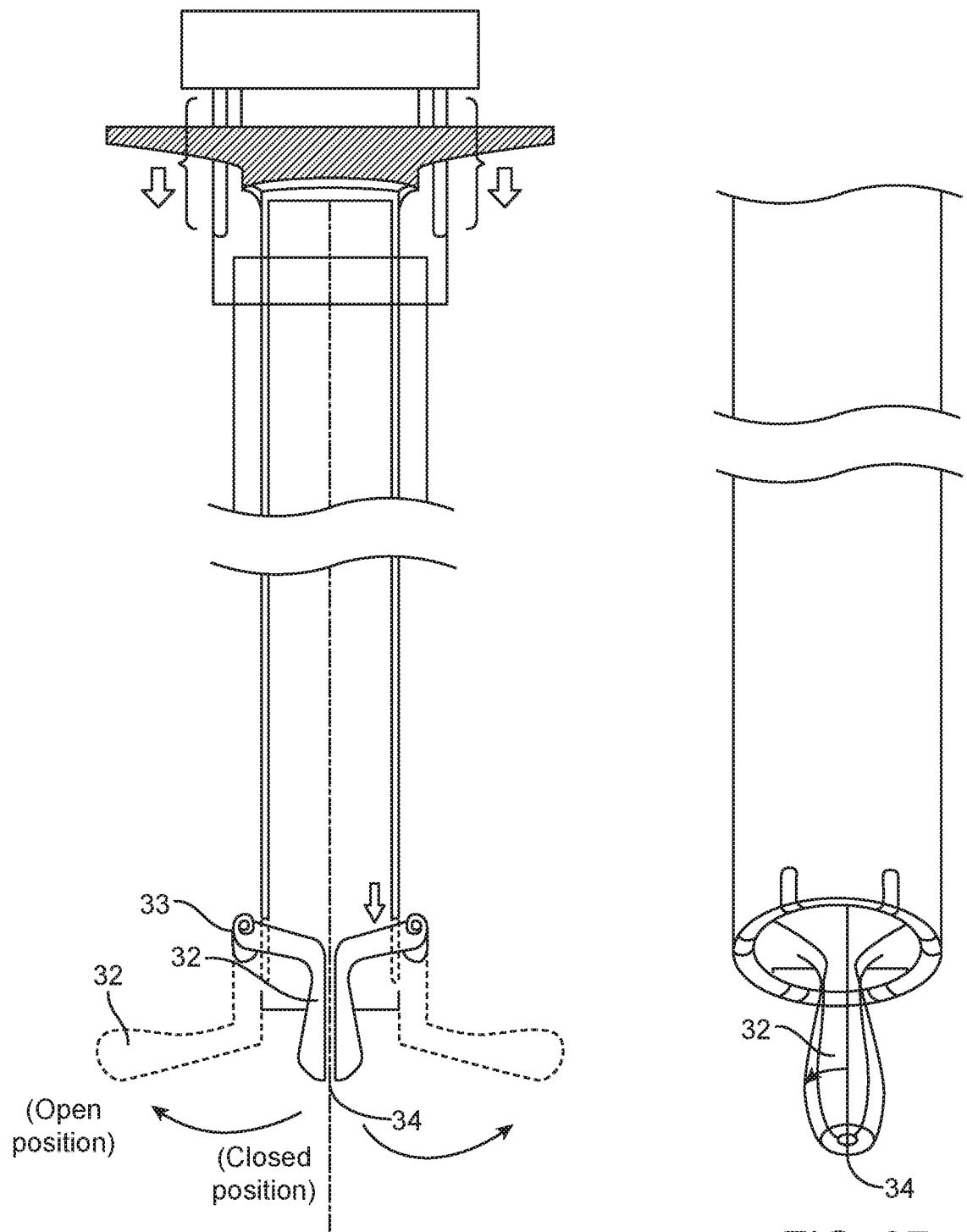

APPLICATORS FOR MODULAR MAGNETIC ANASTOMOSIS DEVICE

CROSS-REFERENCE

This application is a National Stage Entry of International Patent Application PCT/IB2013/003246, filed Dec. 20, 2013, which claims the benefit of U.S. Provisional Patent Application No. 61/740,865, filed Dec. 21, 2012, and U.S. Provisional Patent Application No. 61/794,782, filed Mar. 15, 2013, each of which is incorporated herein by reference in its entirety.

BACKGROUND OF THE INVENTION

The present invention relates to an applicator and methods particularly useful for the delivery of injection medical devices by minimally invasive single site surgery (MISS), natural orifice transluminal endoscopic surgery or colonoscopic surgery (NOTES™).

In one embodiment, the injection device is a modular magnetic anastomosis device.

In one embodiment, the applicator is a laparoscopic instrument.

In an additional embodiment the laparoscopic instrument has is comprised of:
a) an exterior tube, b) an interior tube, c) a sealing system, d) an actuation system, e) a stowing system.

In one embodiment, an aperture to the organ is performed prior to stowing the applicator.

In another embodiment, an aperture to the organ is performed after fastening the applicator.

In one embodiment, the actuation is performed by a button.

In another embodiment, the actuation is performed by a serrated roller.

In one embodiment, the actuation is ordered by a radial toothed rack.

In another embodiment, the actuation is ordered by handle with a longitudinal toothed rack.

In one embodiment, the actuation is the sliding of an internal tube into an external tube.

In one embodiment, the fastening to the pneumoperitoneum is performed with a set of valves.

In another embodiment, the fastening to the pneumoperitoneum is performed with aspiration.

In one embodiment, the fastening to the pneumoperitoneum is performed with pliers with chuck jaws in either side of the elongated tube with sharp spikes.

In another embodiment, the fastening to the pneumoperitoneum is performed with teeth being curved radially and in an opposite direction at the extremities of internal and external tubes as to grasp the external wall of the digestive tract by simple rotation of these two tubes.

In an alternate embodiment, the fastening to the pneumoperitoneum is performed through a small tooth-needle fixed in the periphery of opposite sites two by two of the internal tubes. A thrust at a right angle slides during the actuation making contact of the internal tube with the external tube, teeth leave their housing, take the deployed form.

In another embodiment, the fastening to the pneumoperitoneum is performed by actuation of the internal tube relative to the external tube which opens and closes a circular network of small grips; the internal tube possesses a regular network of holes by which pass rivets; each rivet communicates between the tubes a the driveshaft articulating two arms interdependent of the external tube where the actuation of the internal tube actuates the network of claws.

In one embodiment, the internal tube and external tube are connected except for the hollow zone linked to an external aspiration device creating under aspiration a circumferential zone stowed to the organ.

In another embodiment, the internal tube and external tube are kept together by a network of rings which allows the aspiration under vacuum to fasten the laparoscopic instrument.

In one embodiment, the extremity of the external tube is divided into flexible arms with final pin with small release in the base.

In one embodiment, by sliding the internal tube inside the external tube deformed elastic arms are pushed radially outwards.

In another embodiment, elastic arms are fixed in the periphery of the external tube as stems of cylindrical section.

In another embodiment, rigid elbows with bent jaws are placed in the periphery of the external tube.

In one embodiment, the anatomical structure is imprisoned between the hooks after rotation of the external and internal tubes.

In one embodiment, the injection medical device is used through colonoscopy.

In another embodiment, the applicator is formed by an internal tube and an external tube with a flange shape base and both act as a syringe dislodging the device.

In one embodiment, an injection medical device is used as an endoscopy instrument.

In one embodiment, the injection device is enclosed in a flexible cartridge at the extremity of a guide tube.

In another embodiment, the injection device is enclosed in a hollow cylindrical cartridge with a convex flexible extremity.

In one embodiment, the device is fixed to the end of sheath in the extremity of the cartridge.

In another embodiment, a push rod actuates the cable of sheath.

In an additional embodiment, the cable slides the inside piston ejecting the device.

In one embodiment, the device is ejected with a piston.

In another embodiment, the piston is rigid.

In yet another embodiment, the piston is flexible.

BRIEF DESCRIPTION OF THE DRAWINGS

FIGS. 19 and 20; describe a laparoscopic applicator that the stowing system comprises a network of small tooth-needles.

FIGS. 21 and 22; illustrate introduction of tooth-needle and deployed form of the tooth-needle after the laparoscopic applicator is fixed to desired anatomic surface.

FIGS. 26, 27 and 28; describe a laparoscopic applicator which is applied against the surface to be deployed by aspiration.

FIG. 29; illustrates an applicator with exterior and interior tubes in contact with series of rings.

FIGS. 36 and 37; illustrate an applicator with rigid articulate hooks.

DETAILED DESCRIPTION OF THE INVENTION

Figure 1:
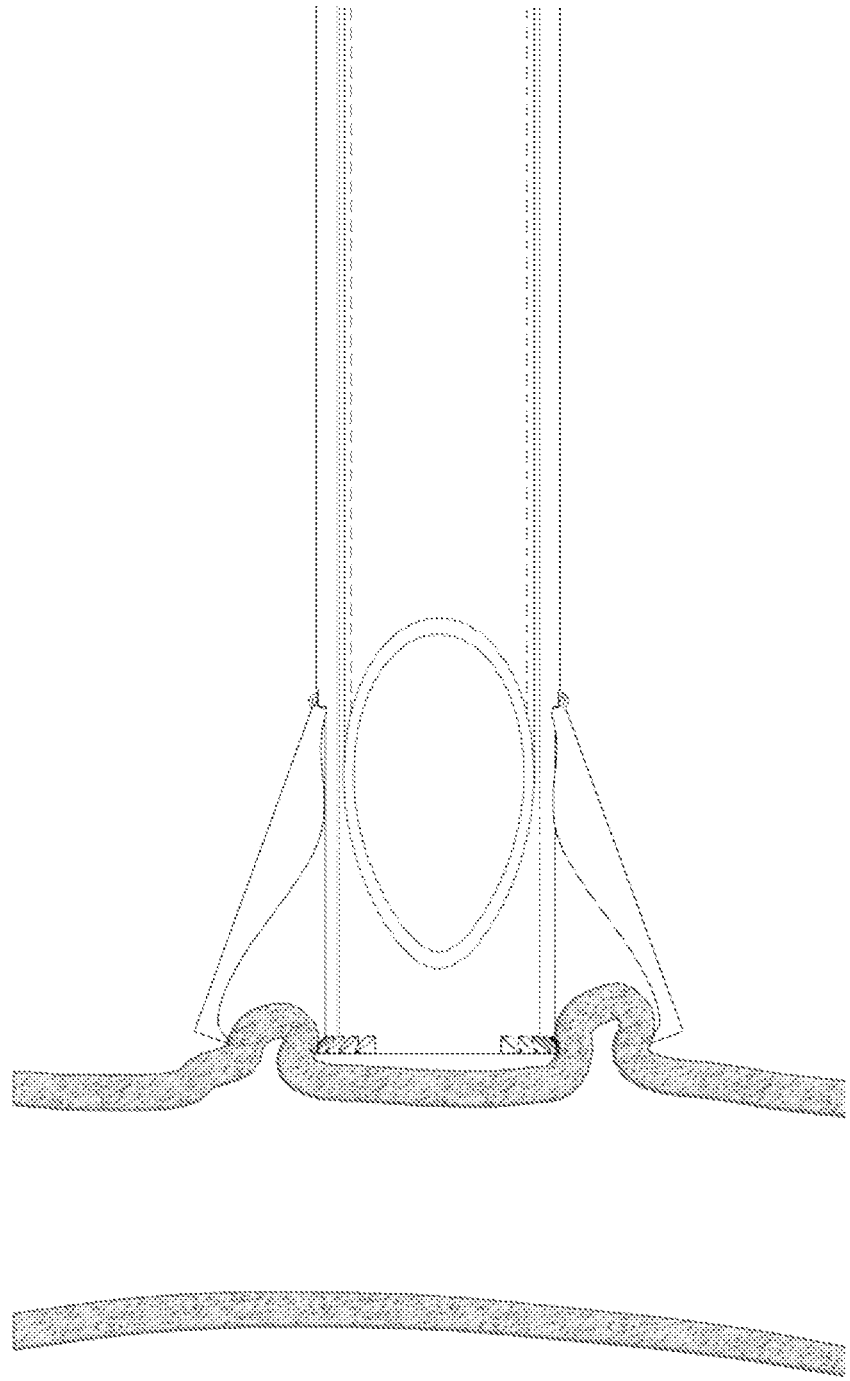
FIG. 1; illustrates an applicator for a modular magnetic anastomosis device using a laparoscopic technique with tightness valves for maintaining the pneumoperitoneum.
Figure 2:
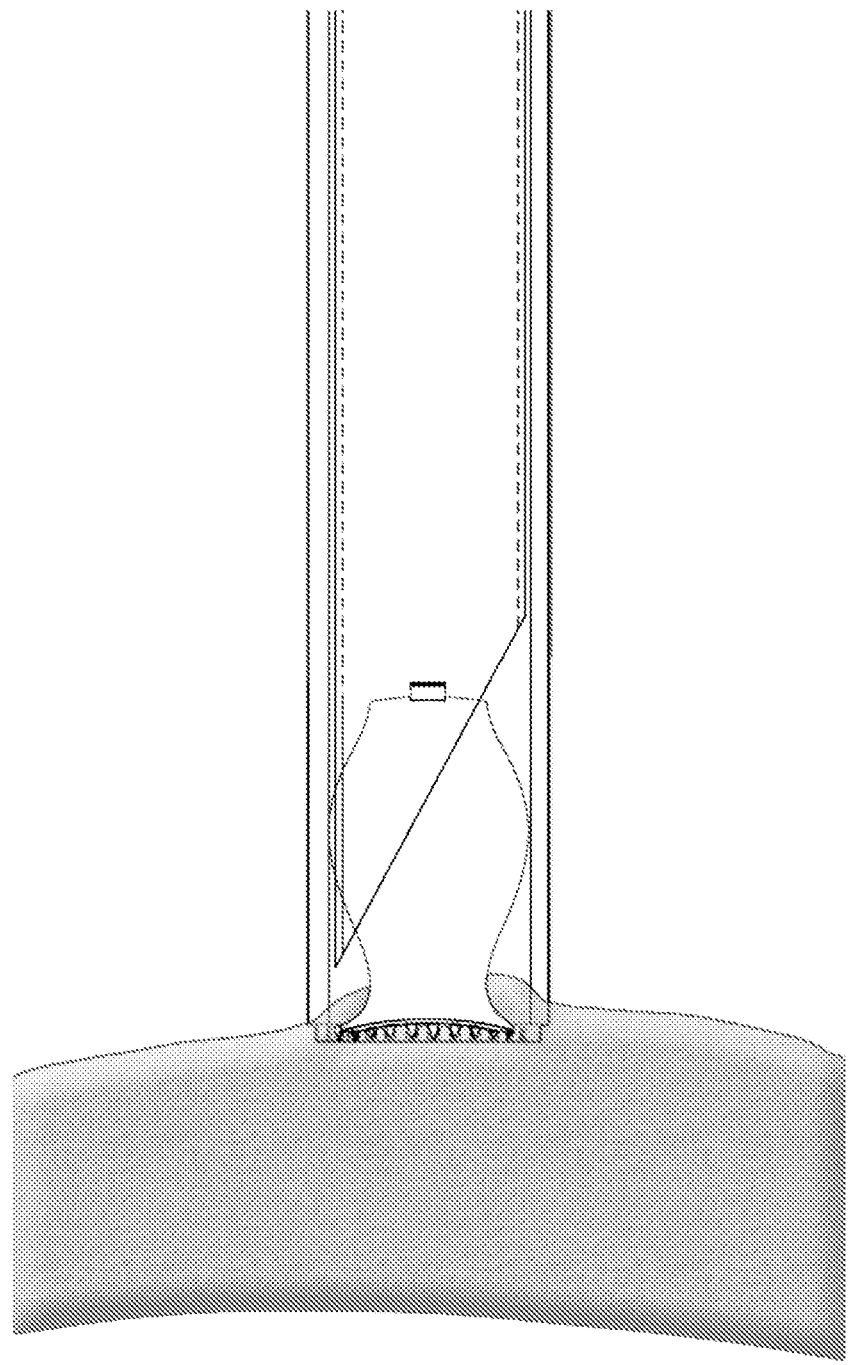
FIG. 2; is a side view of the laparoscopic applicator of the modular magnetic anastomosis device.
Figure 3:
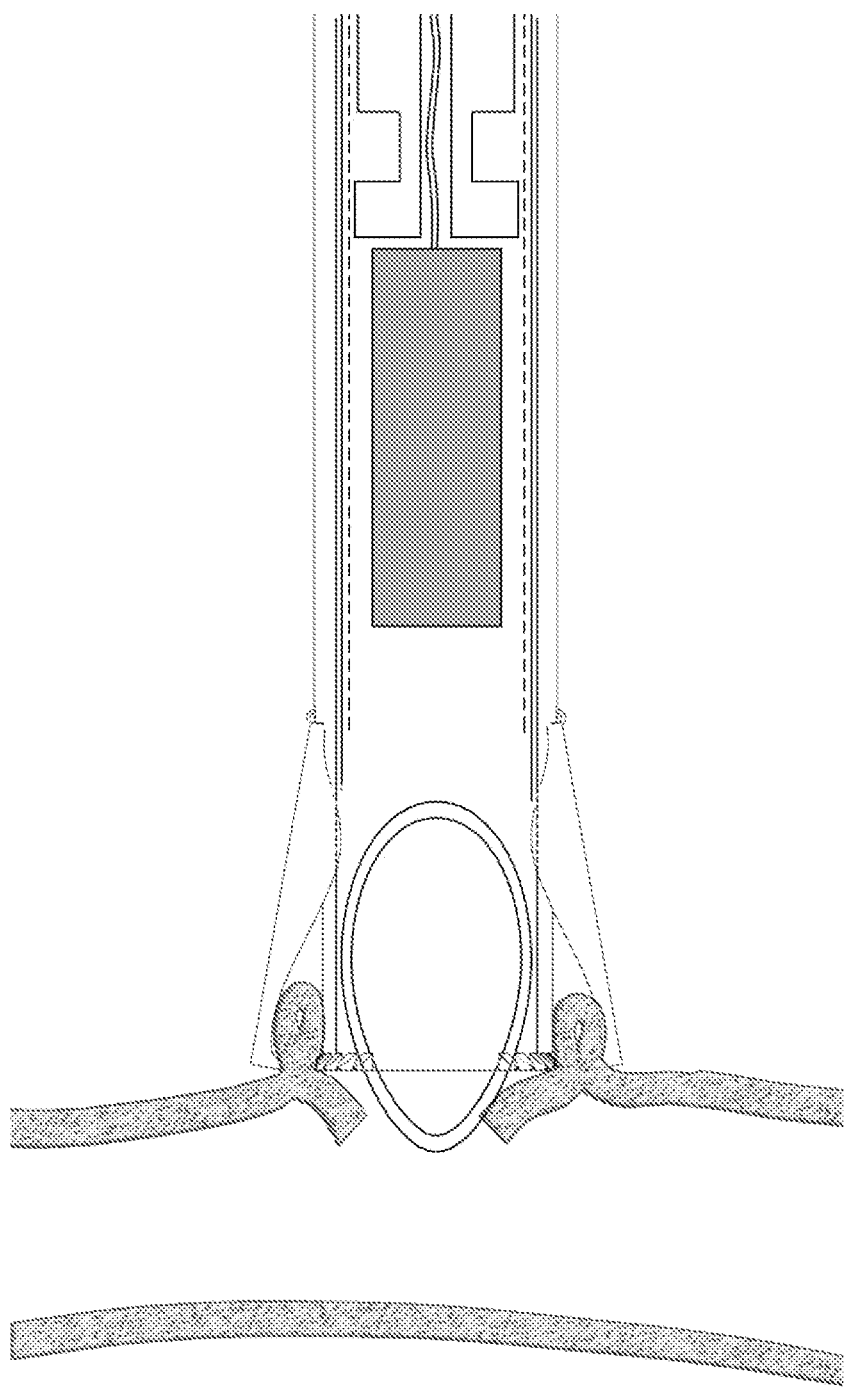
FIG. 3; describes a cross longitudinal perspective of the main body of the applicator, with the second beveled and sharpened tube and the arrangement of modular magnetic anastomosis device inside of the second glide tube.

Minimally invasive single site surgery (MISS) or natural orifice transluminal endoscopic surgery (NOTES™) are terminologies to explain the novel concept of scarless surgery which are increasingly making their way into clinical practice. Laparoscopic and endoscopic surgeries are well-established alternatives to open surgery for anastomosis. In general, the benefits of laparoscopy and endoscopy on postoperative pain, cosmetic benefits, hospital stay and convalescence are widely recognized. Central to the performance of MISS or NOTES surgery is the ability to achieve efficient and effective access to the surgical area of interest via a single port of entry using an endoscopic, percutaneous or laparoscopic applicator.

The MISS surgery approach has the potential to advance the field of percutaneous intra- and transluminal surgery. By direct percutaneous entry into hollow organs such as the urinary bladder, stomach and colon, newer intra- and transluminal procedures could be developed. The potential advantages of this approach would include operating within a localized pneumoviscerum environment (e.g., pneumovesicum, pneumogastrum or pneumocolum) in contrast to a generalized pneumoperitoneum, thereby potentially allowing certain major abdominal procedures to be performed under regional rather than general anesthesia.

The development priorities to meet future needs of MISS surgery are evenly divided across four categories: ports, instruments, optics and robotics. Of late, there has been a new entry to MISS surgery platforms: Single-Port Instrument Delivery Extended Research (SPIDER™ developed by TransEnterix Inc., Research Triangle Park, N.C., USA). It has been proposed that by instrument manipulation past the level of the skin and fascia, the local wound inflammation would be minimized compared with standard laparoscopy. Surgeons from IRCAD, Strasbourg, performed the first transvaginal NOTES™ cholecystectomy in humans in 2007. Since then, many NOTES™ procedures have been performed for varied indications using one or two instruments for dissection and retraction introduced through the transumbilical rigid trocars. They are primarily labeled as "Hybrid-NOTES." It is a win-win situation for both of these surgical access techniques (MISS and NOTES™) as they compensate for the disadvantages of each other and still adhere to the concept of "scarless" surgery.

The use of laparoscopic tools can not only help avoid trauma by decreasing removal and reinsertion but can also reduce the number of incision required to perform a procedure. They also reduce the additional time that is not directly spent in helping the patient in the operating room (OR) and thus reduce the patient risk and costs. Jamshidi et al. demonstrated the safety and efficacy of magnetic compression anastomosis (magnamosis) devices for sutureless, full-thickness intestinal anastomosis with serosal apposition and without leaks in a pig model. They further comment that gradient compression is superior to uniform compression. Mechanical integrity of magnetic anastomosis was similar to, if not better than staple or suture counterparts. Endoscopically placed tick internal magnets with external magnetic guidance is a feasible and novel approach to creating gastroenteral anastomosis without abdominal incisions or sutures.

The IRCAD institute has developed a modular magnetic anastomosis device; the installation of the device requires a limited access compared to its useful surface after deployment. It can be placed accurately and in a minimally invasive fashion in any segment of the digestive tract; it allows realizing bypasses between all hollow viscera; it is also available in all useful sizes by the simple addition of magnetic elements according to the anatomical structure on which it has to be implemented. In its non-deployed shape, the system can be placed inside a small sized channel. It can be placed on a guide-tread and inserted into an access device such as a catheter.

The present invention relates to an applicator and methods particularly useful for delivery of injection medical device in a minimally invasive single site surgery (MISS), natural orifice transluminal endoscopic surgery or colonoscopy surgery (NOTES™).

The laparoscopic instruments are functioning as a hopper. In contact with the surface to be deployed, the hopper preserves the pressure on the pneumoperitoneum; using standard instruments before or after stowing according to the alternatives aperture is created; and the device is introduced to the internal organ by a flexible or rigid piston according to the alternatives. The upper parts of these laparoscopic instruments are formed in a similar fashion and a set of valves ensures the sealing and the conservation of the pneumoperitoneum; except for the alternatives presented in FIGS. 26 to 29, where the fixation is assured using aspiration. The principal structure of the alternatives are two tubes: one internal tube enveloped by an external tube with radial or longitudinal relative movement; wherein the relative movement is ordered by a button, a serrated roller or a handle actuating a radial or longitudinal toothed rack; or simply by manual sliding motion of the two tubes as represented in FIGS. 30 to 35. The sliding motion of the external and interior tubes actuates various mechanism of fixation located at the end of the device.

Figure 4:
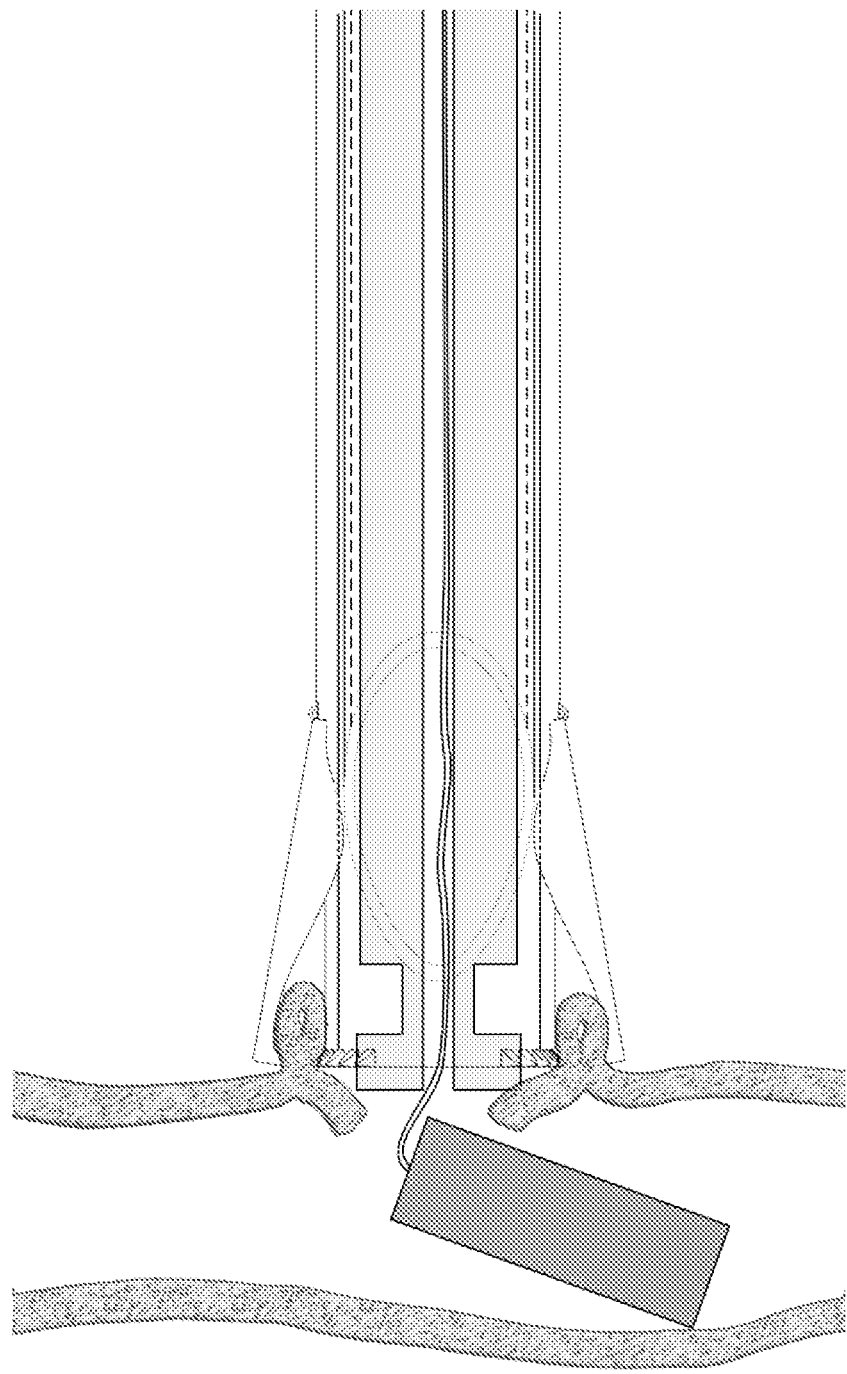
FIG. 4; illustrates the ejection of the anastomosis device with the wire guide from the laparoscopic applicator in the non-deployed configuration.

FIG. 1 to FIG. 4 present one variant of an applicator for the modular anastomosis device; where the delivery instrument is a laparoscopic applicator with an extremity possessing tightness valves maintaining the pneumoperitoneum for inserting or retrieving the various parts of the anastomosis device or tools for the procedure. The main body of the applicator 1.4 is an elongated tube; pliers with chuck jaws are placed on either side of the elongated tube, presented in FIGS. 1.2 and 2.2. The extremity of this elongated tube possesses sharp spikes acting as intermediary chuck jaws for the pliers 1.1 and 3.1. A second beveled and sharpened tube is presented in 1.3, 2.3 and 3.3; this second tube glides inside the first one and is used to cut the wall. The modular anastomosis device is logged into the second tube illustrated in 3.6 and is ejected to the organ to be deployed using a plunger presented in 3.5. FIG. 4 illustrates the modular magnetic anastomosis device with the wire guide ejected from the laparoscopic applicator.

Figure 5:
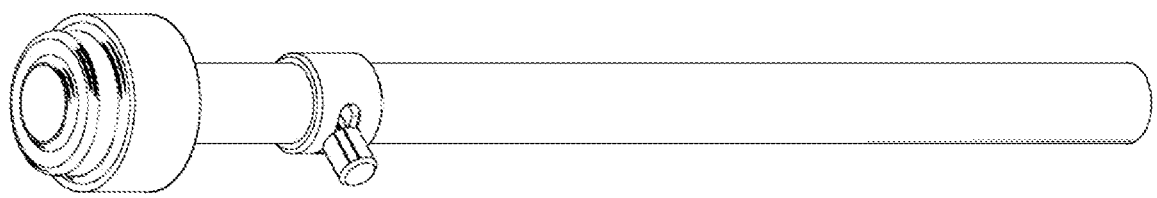
FIG. 5; describes a variant of the laparoscopic applicator where the main body of the applicator and the internal tube are fitted together with a tightness valve and an external button for opening and closing the applicator.
Figure 6:
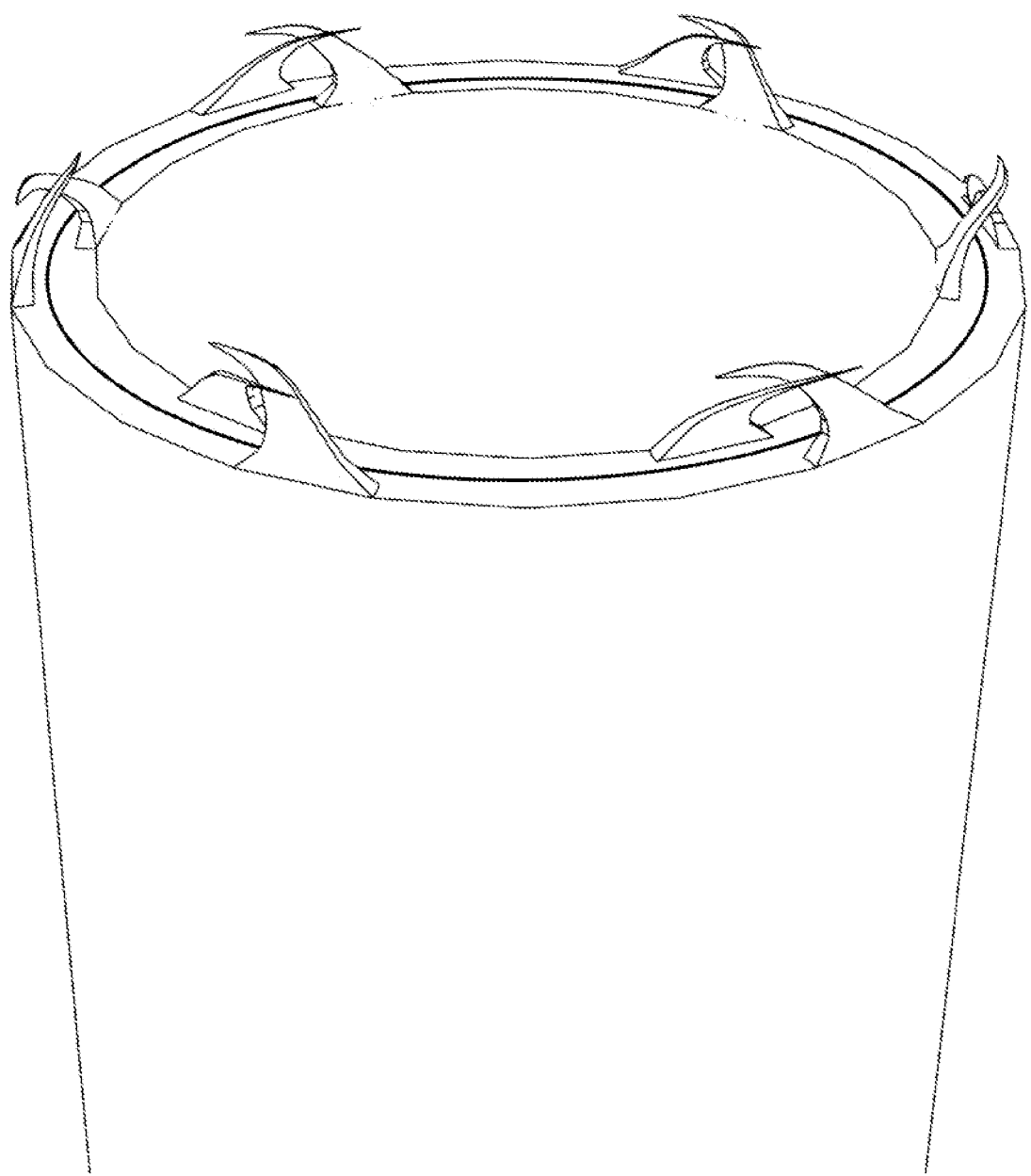
FIG. 6; shows a cross section of the main body of the applicator fitted with the internal secondary tube with teeth being curved radially and in opposite direction.
Figure 7:
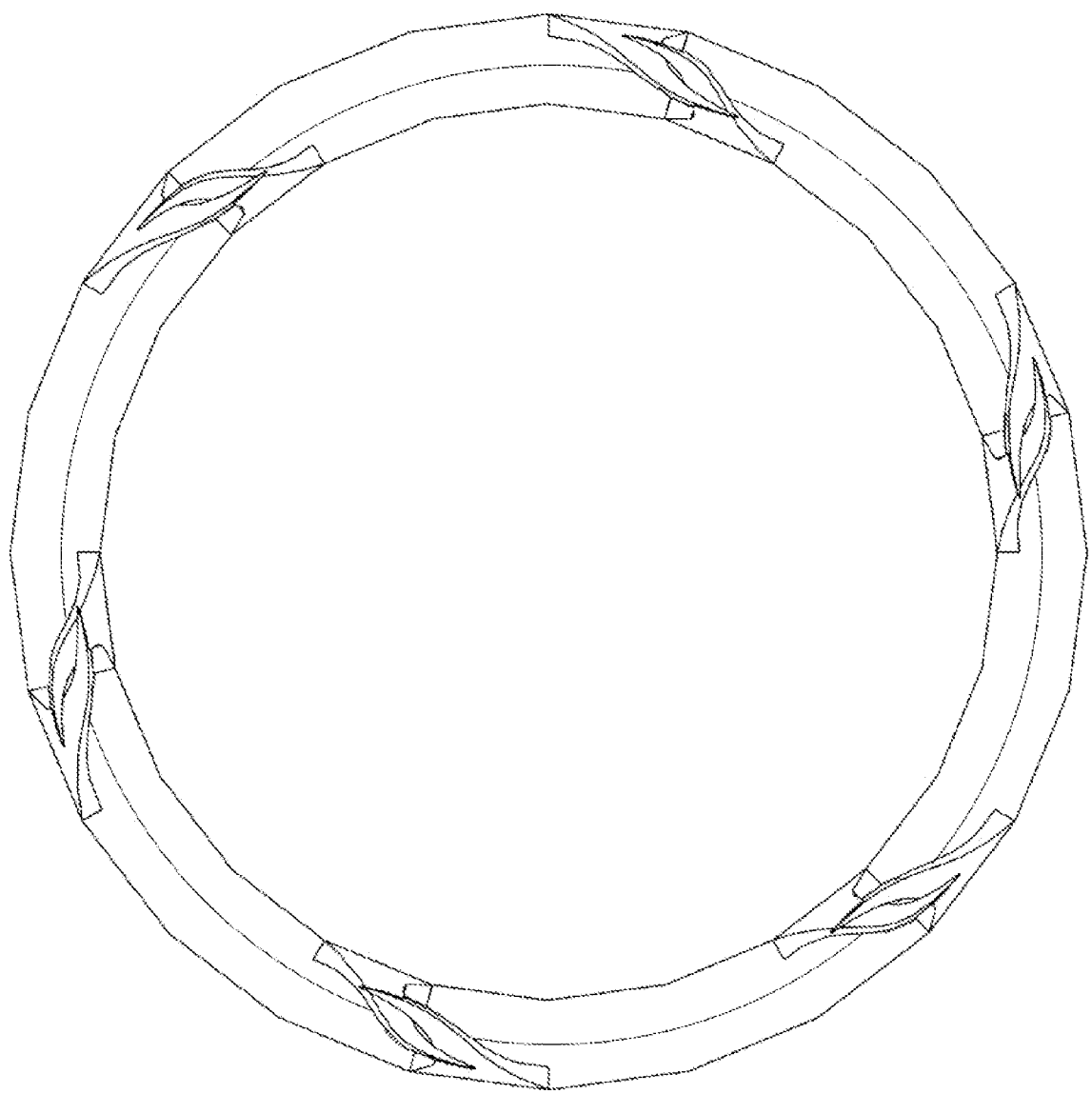
FIG. 7; is a presentation of the interaction between the teeth of the main body and the second internal tube of the applicator.
Figure 8A:
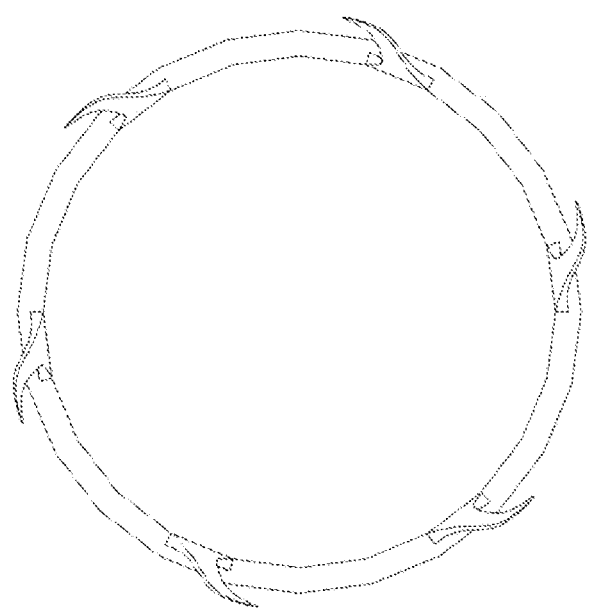
FIG. 8A-B; shows separately inner and outer tubes with general orientation of teeth.
Figure 8B:
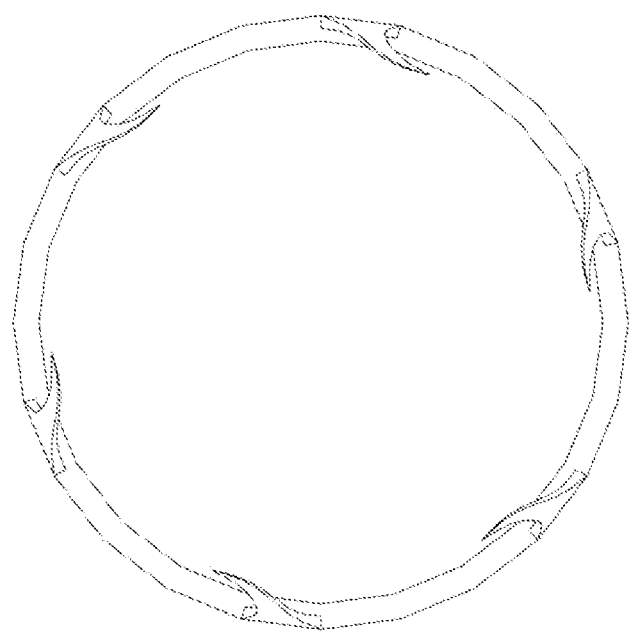

In a different variant, the laparoscopic applicator possesses a main body with a second internal tube fitted together. FIG. 5 illustrates this form of the device; 5.1 presents the basis with tightness valves allowing to maintain the pneumoperitoneum for insertion or retrieving the various parts of the modular anastomosis device or tools used to carry out the procedure. FIG. 6 shows the main body of the applicator 6.1, and the internal tube is shown in FIG. 6.2. Extremities of both of these tubes are teeth 6.3 being curved radially and in an opposite direction as to grasp the external wall of the digestive tract by simply rotating both tubes represented in FIG. 7. The teeth are maintained in a closed position with a blocking mechanism using springs or tension ribbons resisting to the opening of the applicator jaws shown in 8.1 and 8.2. The open and closed positions of the applicator are maneuvered by a button or a handle on the external part of the applicator, as illustrated in 5.2.

Figure 9:
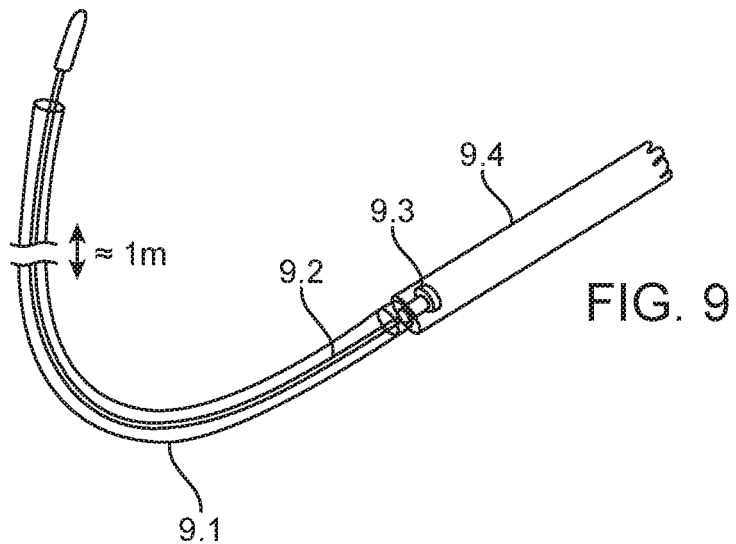
FIG. 9; shows the modular magnetic anastomosis device applicator used in endoscopy with the flexible cartridge enclosing the device.
Figure 10:
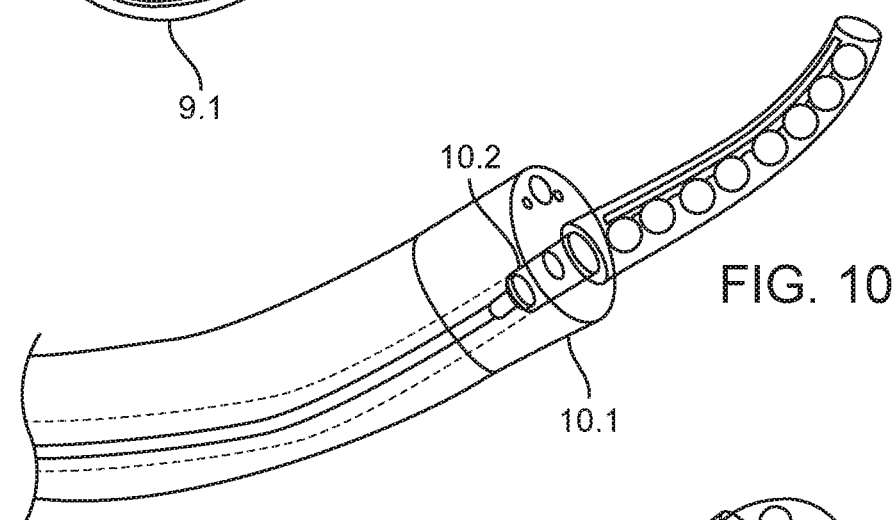
FIG. 10; illustrates the presence of the applicator used in an endoscope.
Figure 11:
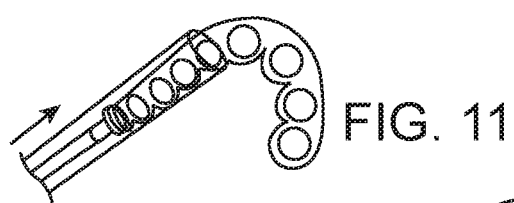
FIG. 11; shows the plunger pushing and thus ejecting the modular magnetic anastomosis device out of the flexible cartridge of the endoscopic applicator.
Figure 12:
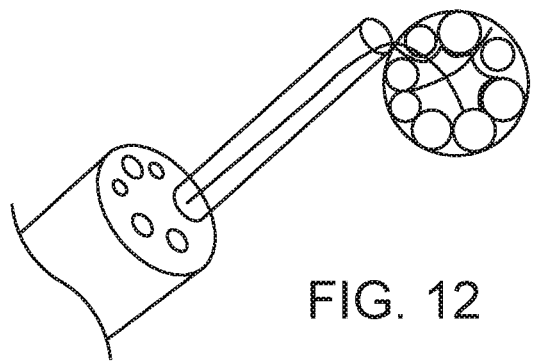
FIG. 12; presents the anastomosis device in its deployed configuration using the wire guide to close the device.

The non-deployed modular magnetic anastomosis device requires limited access compared to its useful surface after deployment, and it can be placed inside a small sized channel and be used by being inserted into an operating channel of the endoscope. FIG. 9 illustrates the various parts of such an applicator, composed of a guide tube 9.1 which is placed inside the operating channel of the endoscope to which is fitted a flexible cartridge 9.4 which encloses the modular magnetic anastomosis device. The device is deployed in the transplant organ by injecting it out from the flexible cartridge via a plunger 9.3 that is moved using a cable 9.2. FIG. 10 describes an endoscope 10.1 and the channel 10.2 with the cartridge ejected. FIGS. 11 and 12 illustrate the ejection of the anastomosis device from the cartridge and the final deployed circular modular magnetic anastomosis device.

Figure 13:
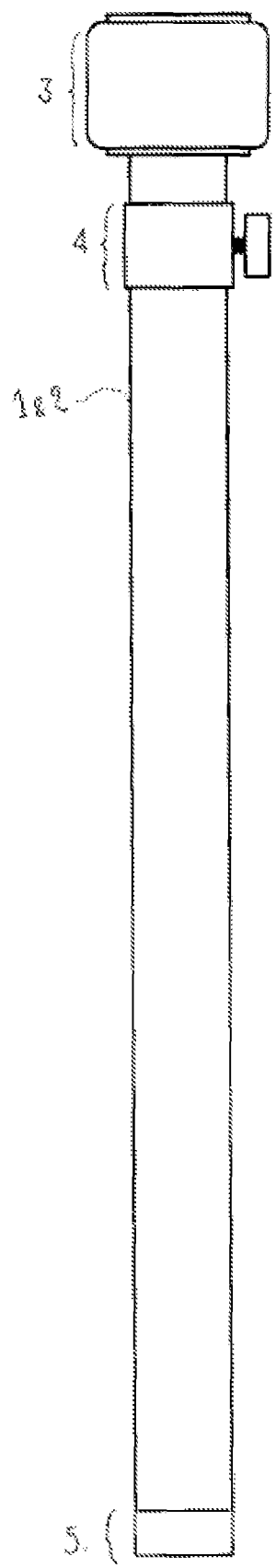
FIG. 13; illustrates general structure of a laparoscopic applicator for a modular magnetic anastomosis comprises:
(1) exterior tube
(2) interior tube
(3) sealing system
(4) actuation system
(5) stowing system FIG. 14; is the cross longitudinal perspective of the main body of the applicator.
Figure 14:
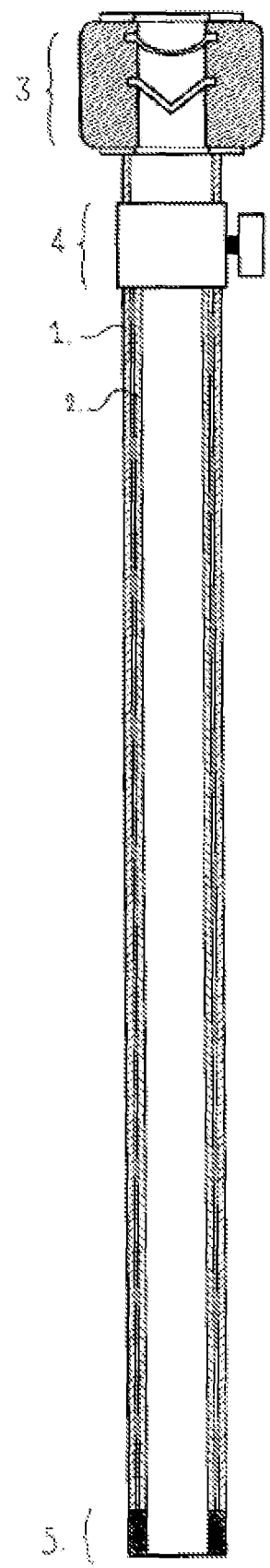

A general structure of a laparoscopic applicator is described in FIG. 13 formed by an exterior tube (1), interior tube (2), sealing system (3), actuation system (4), stowing system (5); FIG. 14 is a cross longitudinal view of the applicator.

Figure 15:
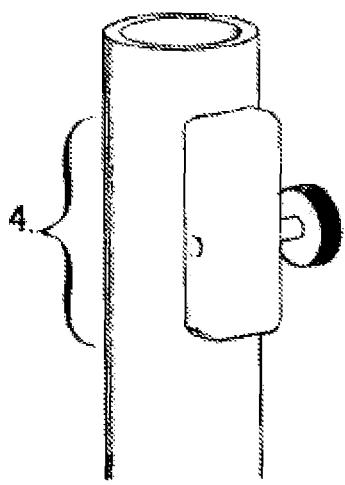
FIG. 15; illustrates external view of actuation system.
Figure 16:
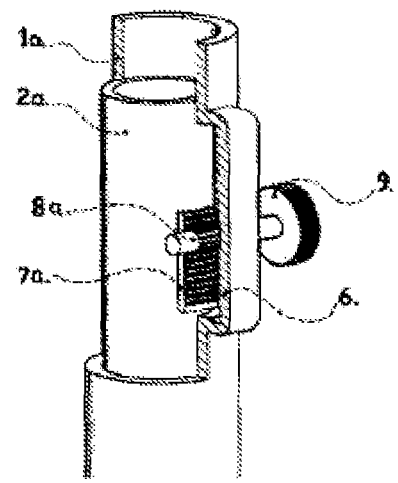
FIG. 16; describes a cross longitudinal view of the actuation system with different components that operate the mechanical movement and rotation of serrated roller.
Figure 17:
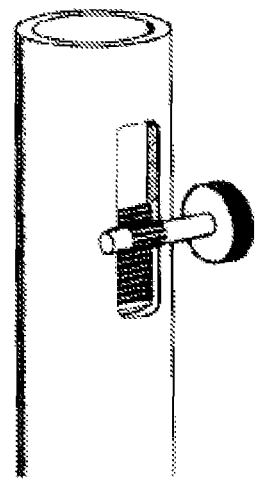
FIG. 17; illustrates different components that operate the mechanical movement and rotation of the serrated roller.
Figure 18:
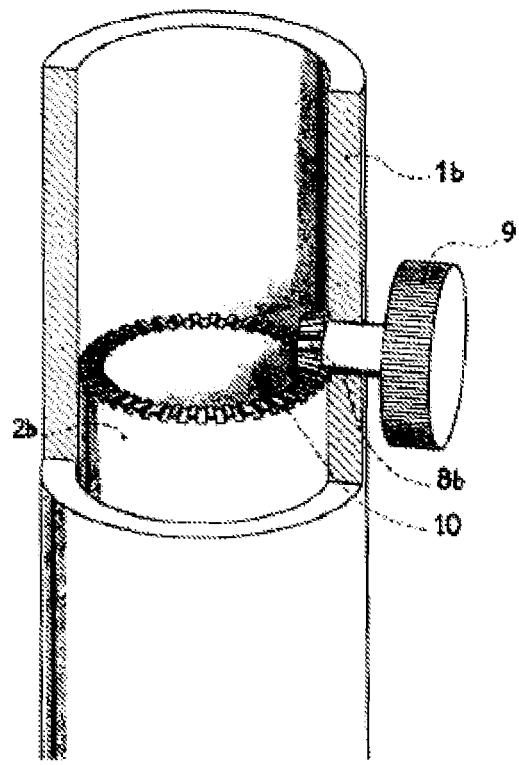
FIG. 18; illustrates an alternative form of serrated roller.

A structure of one of the actuation systems is described in FIGS. 15, 16 and 17, wherein the different components that operate the actuation system (4) make a translational movement between (1a) and (2a) by the rotation of serrated roller (9). In an alternative structure of the actuation system, presented in FIG. 18, the rotational movement between (1b) and (2b) by the rotation of the serrated roller (9) and a truncated end (8b) on the toothed circular section (10) is illustrated.

One variant of a stowing system (5) is described in FIGS. 19 and 20, where the attachment system is through a network of small tooth-needles (11) fixed in the periphery of opposite sites two by two (14) of the internal tube (2a) a thrust at an right angle (12) slides during the actuation of the serrated roller (9) in small release (13) forming the end (15) of the external tube (1a). The contact of the extremities of the internal tube (14) with the external tube (15); teeth (11) leave their housing (13), take the deployed form presented in FIGS. 21 and 22 and for two by two the interior loops clutched to the organ to be fastened.

Figure 23:
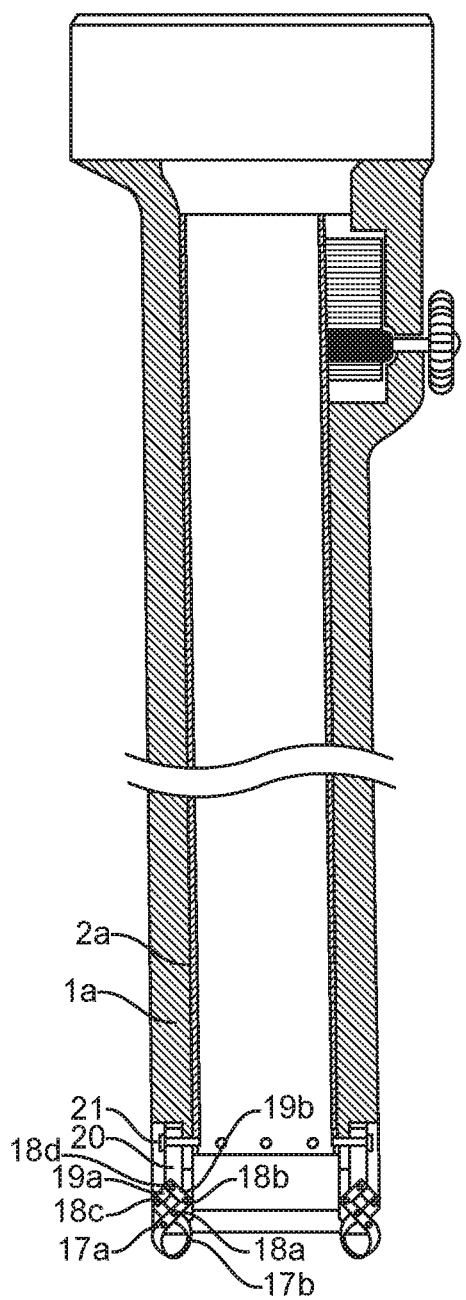
FIGS. 23, 24 and 25; present a laparoscopic applicator where the mechanical movement after stowing the application to desired organ opens and firm a circular network of small grips.
Figure 24:
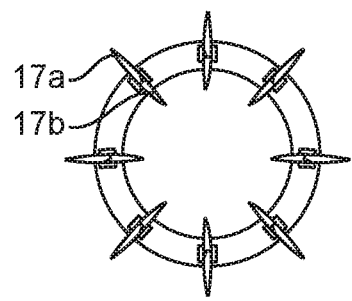
Figure 25:
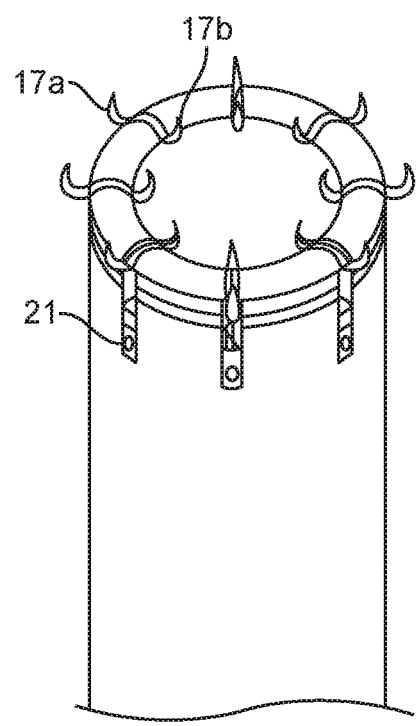
Figure 30:
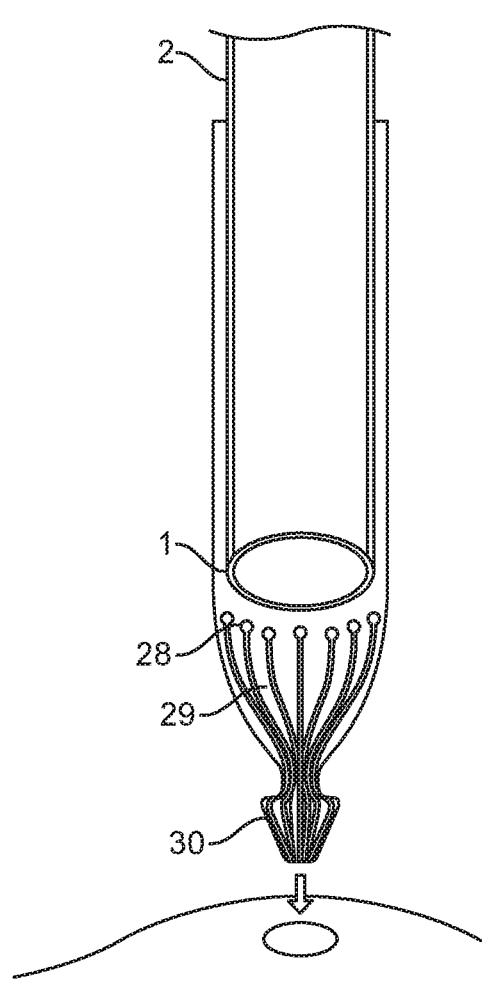
FIGS. 30 and 31; illustrate an applicator with an extremity divided in several resilient flexible or non ferromagnetic metal arms with final spur.
Figure 31:
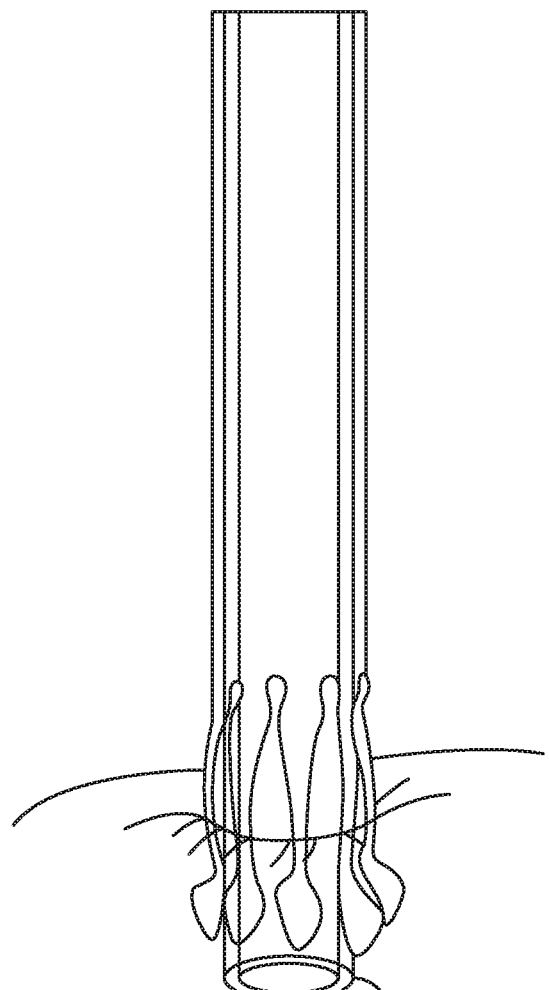
Figure 32:
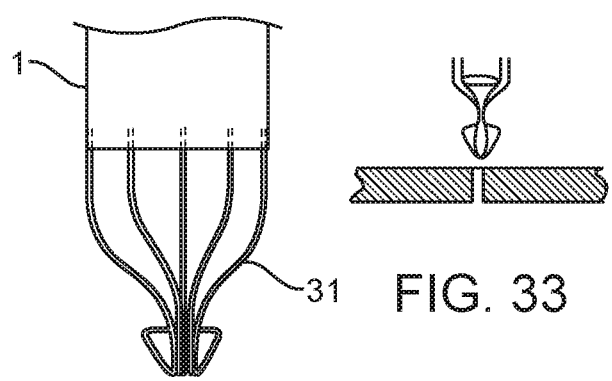
FIG. 32; illustrates the applicator that possessing stems of cylindrical sections allowing the fixation of the laparoscopic applicator after entry.

The change in stowing part (5) in another variant is presented in FIGS. 23, 24 and 25, wherein the actuation of the internal tube (2a) compared to the external tube (1a) opens and closes a circular network of small grips. The extremity of the internal tube (2a) possess a regular network of holes by which rivets pass (21); each rivet communicates between the internal tube (2a) and the driveshaft (20). The arm (20) articulates two intermediate arms (19a) and (19b) on the axis (18d); these two grip (17a) and (17b) are constrained in the axis of rotation (18a), which is interdependent of the external tube (1a); in addition they are connected to the arms (19a) and (19b) by rivets (18b) and (18c); displacement of the internal tube (2a) jointly moves the grips (17a) and (17b) and actuates the network of claws.

In a variant of a laparoscopic device the attachment to the organ is assured by a mechanism of aspiration under vacuum. FIGS. 26, 27, 28, and 29 illustrate such an applicator; the figures describe a unique tubular structure (1d) that replaces the internal and external tubes; a hollow zone (23) linked to a nozzle (22) linked to an external aspiration tube connected to an external device; the extremity of the device (24) under aspiration on a circumferential zone is fixed to the surface to be stowed. FIG. 29 shows the variant with external and internal tubes (1c) and (2c) that are maintained in position by a network of rings (25), which are bored with holes (26) allowing the aspiration under vacuum.

Figure 33:
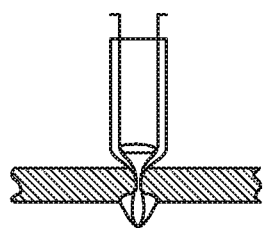
FIGS. 33, 34 and 35; illustrate the deployed form of laparoscopic applicator describe in FIGS. 30 and 31 and 32.
Figure 34:
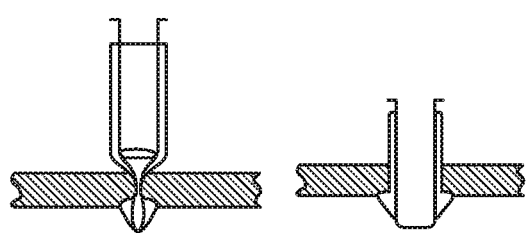
Figure 35:
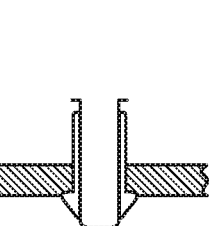

In another variant of a laparoscopic applicator the aperture for the surgery is carried out in the anatomical organ before fastening the applicator. FIGS. 30 to 35 describe such an applicator; the extremity (1) is divided into several flexible arms (29) with a final pin (30); the small release (28) in the base of (29) guarantees the flexibility of the spacing and the distal pin (30) is inserted in the opening. The actuation process is the sliding of tube (2) into the external tube (1); the arms (29) become deformed elastically and are pushed back radially by tube (2) in order to fasten this applicator to the anatomical structure. An alternative is presented in FIG. 32, where the elastic arms (31) are stems of cylindrical sections, fixed (1) by any means useful and performed to achieve the same function. FIGS. 33, 34 and 35 describe the operational mode.

A variant of the previous applicator wherein the elastic strains are replaced with rigid elbows is described in FIGS. 36 and 37. In this alternative mode, several bent jaws (32) are fixed to the external tube (1). By a combination of rotation (33) and sliding of the internal tube (2), tube (1) pushes back (32) radially toward the outside and is fastening the instrument to the desired organ.

The geometry of the two tubes (32) induces a closed position and a central nozzle (34) allows the sliding of a wire-guide.

Figure 40:
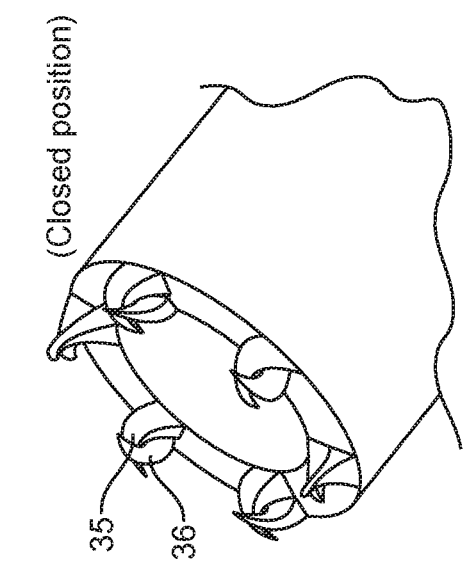
FIGS. 38, 39 and 40; represent laparoscopic applicator that external and interior tubes of the applicator are fitted together with teeth being curved radially and in opposite direction.
Figure 39:
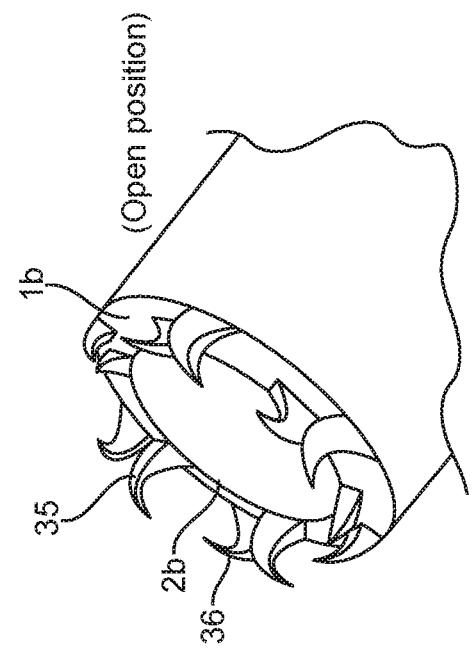
Figure 38:
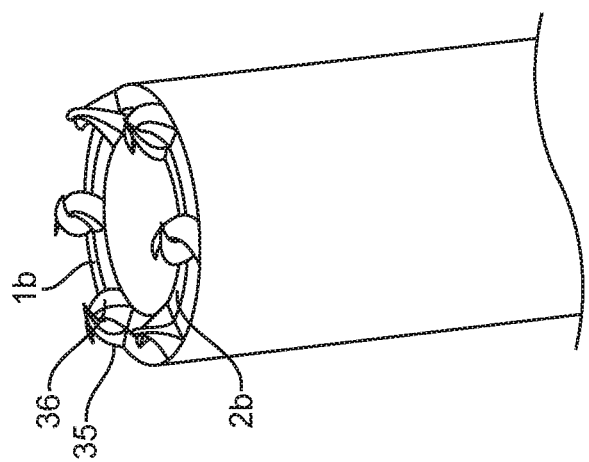

A variant of an laparoscopic applicator wherein said applicator is attached to the surface before opening an aperture, is depicted in FIGS. 38, 39 and 40; the external tube (1b) and internal tube (2b) with a rotational move as illustrated in FIG. 38; extremities of the tubes (1b) and (2b) possess a circular network with an equal number of small hooks, respectively (35) and (36) bent one towards the other in such a way that actuation in rotation (2b) relative to (1b) seizes and imprisons the anatomical structure to which the applicator is fastened.

Figure 41:
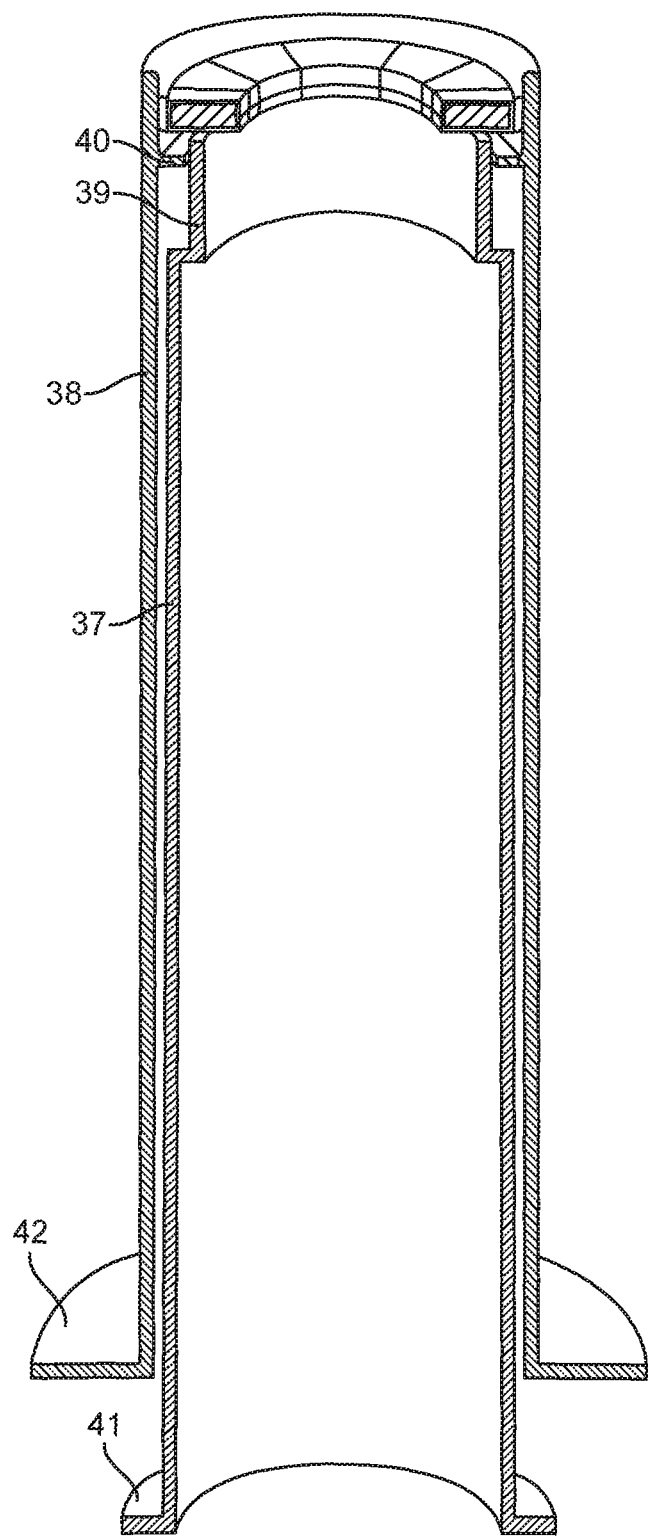
FIG. 41; describes a colonoscopy applicator for modular magnetic anastomosis.

FIG. 41 presents an alternative applicator for use as a magnetic anastomosis device such as described in WO2013/009886 A1 using a natural orifice, such as the colon. This applicator is formed by an internal tube (37) and an external tube (38); their bases in the shape of a flange (41) and (42) to allow the sliding of (37) in (38) such as in a syringe and dislodging the anastomosis device; a boring (40) in the interior of (38) retains the anastomosis device in a functional position; the push of (41) towards (42) resulting in the ejection of the anastomosis device and tightening (39) at the end of the internal tube.

Figure 42:
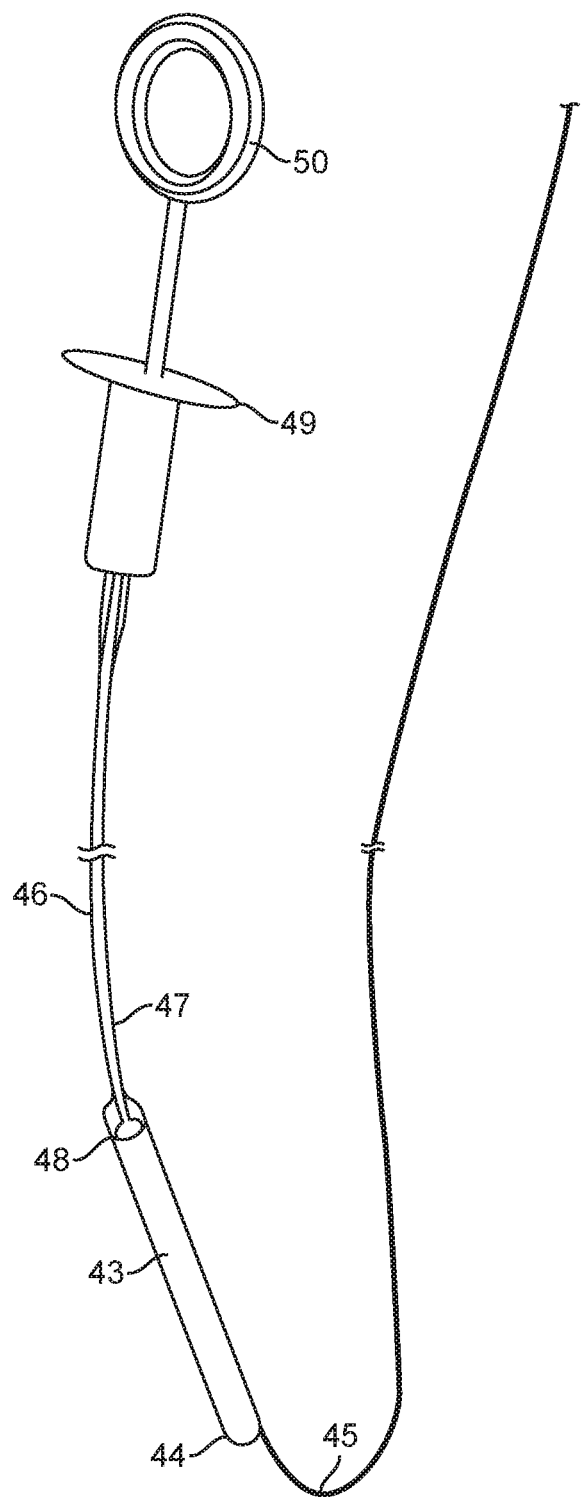
FIG. 42; shows a variant of modular magnetic anastomosis device applicator used in endoscopy with the flexible cartridge enclosing the device.

FIG. 42 presents an endoscopic variant of the applicator, which consists of a hollow cylindrical cartridge (43) with a convex extremity enclosing the device to be released; a flexible and extensible opening (44) is at the extremity of the cartridge (43) which is fixed to the ending (49) of a sheath (46), in this sheath circulates a cable (47) by actuating a push rod (40); the cable (47) slides the piston (48) inside of (43) ejecting the device contained in (43).

What is claimed is:
1. A surgical system comprising:
(a) a modular magnetic anastomosis device; and
(b) an applicator for delivery of the modular magnetic anastomosis device to an organ, the applicator comprising:
(i) a first elongated tube comprising a hollow lumen connecting a proximal end and a distal end, wherein the distal end comprises elastically deformable arms that and form an elastically deformable pin configuration;
(ii) a second elongated tube that is enveloped by the first elongated tube and comprises a hollow lumen configured to receive the modular magnetic anastomosis device; and
(iii) a sealing system comprising a valve which is configured to prevent air from escaping through the applicator when the applicator is placed into the peritoneal cavity and a peritoneal cavity is insufflated with air;
wherein the second elongated tube is configured to slide relative to the first elongated tube and is positioned so that a sliding of the second elongated tube in the direction of the distal end causes the elastically deformable arms of the first elongated tube to radially expand thereby deforming an elastically deformable pin configuration so that the elastically deformable arms are pushed back towards an area surrounding the aperture and thereby fastening the applicator to a surgical area of interest;
wherein the modular magnetic anastomosis device is positioned within the second elongated tube so that when the applicator is fastened to the surgical area of interest and the elastically deformable arms are radially expanded, the modular magnetic anastomosis device passes through the second elongated tube to the organ.

2. The surgical system of claim 1, wherein the applicator comprises a laparoscopic instrument.

3. The surgical system of claim 1, wherein the second elongated tube is configured to slide relative to the first elongated tube when a button is pressed.

4. The surgical system of claim 1, wherein the second elongated tube is configured to slide relative to the first elongated tube when a handle actuating a radial toothed rack is moved.

5. The surgical system of claim 1, wherein the second elongated tube is configured to slide relative to the first elongated tube when a handle actuating a longitudinal toothed rack is moved.

6. The surgical system of claim 1, wherein the modular magnetic anastomosis device is configured to be delivered through a natural orifice.

7. The surgical system of claim 1, wherein the modular magnetic anastomosis device comprises an endoscopic instrument.

8. The surgical system of claim 1, comprising a piston formed from a rigid material.

9. The surgical system of claim 1, wherein the elastically deformable arms comprise resilient non-ferromagnetic metal.

10. The surgical system of claim 1, wherein the elastically deformable arms have a conical shape.

* * * * *